United States Patent
Shchepinov

(10) Patent No.: US 9,320,289 B2
(45) Date of Patent: Apr. 26, 2016

(54) ISOTOPICALLY MODIFIED COMPOUNDS AND THEIR USE AS FOOD SUPPLEMENTS

(71) Applicant: RETROTOPE, INC., Los Altos Hills, CA (US)

(72) Inventor: Mikhail Sergeevich Shchepinov, Kingston Upon Thames (GB)

(73) Assignee: Retrotope, Inc., Los Altos Hills, CA (US)

( * ) Notice: Subject to any disclaimer, the term of this patent is extended or adjusted under 35 U.S.C. 154(b) by 0 days.

(21) Appl. No.: 14/551,450

(22) Filed: Nov. 24, 2014

(65) Prior Publication Data

US 2015/0147457 A1    May 28, 2015

Related U.S. Application Data

(62) Division of application No. 12/281,957, filed as application No. PCT/GB2007/050112 on Mar. 8, 2007, now Pat. No. 8,906,405.

(30) Foreign Application Priority Data

Mar. 8, 2006 (GB) .................................. 0604647.8

(51) Int. Cl.
| | |
|---|---|
| A23D 9/00 | (2006.01) |
| A23D 9/007 | (2006.01) |
| A23K 1/00 | (2006.01) |
| A23K 1/18 | (2006.01) |

(Continued)

(52) U.S. Cl.
CPC ...... *A23D 9/007* (2013.01); *A23D 9/00* (2013.01); *A23K 1/007* (2013.01); *A23K 1/188* (2013.01); *A23L 1/30* (2013.01); *A23L 1/3002* (2013.01); *A23L 1/307* (2013.01); *A23L 1/3008* (2013.01); *A23L 1/3012* (2013.01); *A23L 1/3014* (2013.01); *A23L 1/3051* (2013.01); *A23L 1/3053* (2013.01); *A23V 2002/00* (2013.01)

(58) Field of Classification Search
CPC .................................................... A23L 1/3002
See application file for complete search history.

(56) References Cited

U.S. PATENT DOCUMENTS

| 3,520,872 A | 7/1970 | Wechter et al. |
| 5,194,448 A | 3/1993 | Coupland et al. |

(Continued)

FOREIGN PATENT DOCUMENTS

| EP | 1 548 116 A1 | 6/2005 |
| FR | 2 721 518 A3 | 12/1995 |

(Continued)

OTHER PUBLICATIONS

Crombie et al. Synthesis of [14, 14-2H2]—linolenic acid and its use to confirm the pathway to 12-oxophytodienoic acid (12-oxoPDA) in plants: a conspectus of the epoxycarbonium ion derived family of metabolites from linoleic and linolenic acid hydroperoxides. Journal of the Chemical Society, Perkin Transactions 1, No. 3, 1991.

(Continued)

*Primary Examiner* — Benjamin Packard
(74) *Attorney, Agent, or Firm* — Knobbe Martens Olson & Bear LLP

(57) ABSTRACT

A nutrient composition comprises an essential nutrient in which at least one exchangeable H atom is $^2$H and/or at least one C atom is $^{13}$C. The nutrient is thus protected from, inter alia, active oxygen species.

18 Claims, 2 Drawing Sheets

(51) Int. Cl.
  *A23L 1/30* (2006.01)
  *A23L 1/305* (2006.01)
  *A23L 1/307* (2006.01)

(56) References Cited

U.S. PATENT DOCUMENTS

| | | | |
|---|---|---|---|
| 5,843,497 | A | 12/1998 | Sundram et al. |
| 6,111,066 | A | 8/2000 | Anderson, III et al. |
| 6,417,233 | B1 | 7/2002 | Sears et al. |
| 6,503,478 | B2 | 1/2003 | Chaiken et al. |
| 2001/0023259 | A1 | 9/2001 | Slabas et al. |
| 2002/0198177 | A1 | 12/2002 | Horrobin |
| 2006/0035382 | A1 | 2/2006 | Shinozaki et al. |
| 2006/0205685 | A1 | 9/2006 | Phiasivongsa et al. |
| 2006/0241088 | A1 | 10/2006 | Arterburn et al. |
| 2008/0234197 | A1 | 9/2008 | Allam et al. |
| 2009/0069354 | A1 | 3/2009 | Czarnik |

FOREIGN PATENT DOCUMENTS

| | | |
|---|---|---|
| JP | 10-291955 | 11/1998 |
| JP | 2000-290291 | 10/2000 |
| JP | 2001-514239 | 9/2001 |
| JP | 2001-519355 | 10/2001 |
| JP | 2002-513911 | 5/2002 |
| JP | 2002-536981 | 11/2002 |
| WO | WO 2004-029254 | 4/2004 |
| WO | WO 2007/102030 | 9/2007 |
| WO | WO 2009/017833 | 2/2009 |
| WO | WO 2009/114809 | 9/2009 |
| WO | WO 2009/114814 | 9/2009 |

OTHER PUBLICATIONS

Dyall et al, Neurological Benefits of Omega-3 Fatty Acids, Neuromolecular Medicine, vol. 10, No. 4, Jun. 10, 2008.
Evans et al, Endor, triple resonance and ESR studies of spin-trapped radicals in autoxidized linoleic acid and its deuterated derivatives. Biochimica et Biophysica Acta—Lipids and Lipid Metabolism, Elsevier Science BV, Amsterdam, NL, vol. 835, No. 3, Jul. 31, 1985.
Extended European Search Report and Written Opinion dated Jun. 5, 2013 for EP Patent Application No. 10827578.5.
Hussein, N., Long-chain conversion of [13C] linoleic acid and—linolenic acid in response to marked changes in their dietary intake in men, The Journal of Lipid Research, vol. 46, No. 2, Dec. 1, 2004.
Jacquot et al, Isotope Sensitive Branching and Kinetic Isotope Effects in the Reaction of Deuterated Arachidonic Acids with Human 12- and 15-Lipoxygenases +, Biochemistry, vol. 47, No. 27, Jun. 12, 2008.
Johnson et al, Potential role of dietary n-3 fatty acids in the prevention of dementia and macular degeneration, The American Journal of Clinical Nutrition, vol. 83, No. 6, Jun. 2006.
Mazza et al, Omega-3 fatty acids and antioxidants in neurological and psychiatric diseases: An overview, Progress in Neuro-Psychopharmacology & Biological Psychiatry, Oxford, GB, vol. 31, No. 1, Dec. 22, 2006.
Brenna et al; High-Precision Continuous-Flow Isotope Ratio Mass Spectrometry; Mass Spectrometry Review; vol. 16; pp. 227-258; 1997.
Brenna et al; α-Linolenic acid supplementation and conversionton to n-3 long-chain polyunsaturated fatty acids in humans; Prostaglandins, Leukotrienes and Essential Fatty Acids; vol. 80; pp. 85-91; 2009.
Brenna, J.T.; Efficiency of conversion of a-linolenic acid to long chain n-3 fatty acids in man; Lipid Metabolism; pp. 127-132; 2002.
Brenna, J.T.; Use of stable isotopes to study fatty acid and lipoprotein metabolism in man; Prostaglandins, Leukotrienes and Essential Fatty Acids; vol. 57 (4 & 5); pp. 467-472; 1997.
Emken et al; Effect of Dietary Docosahexaenoic Acid on Desaturation and Uptake in vivo of Isotope-Labeled Oleic, Linoleic, and Linolenic Acids by Male Subjects; Lipids; vol. 34, No. 8; pp. 785-791; 1999.

Emken et al; Metabolism of *cis*-12-octadecenoic acid and *trans*-9, *trans*- 12-octadecadienoic acid and their influence on lipogenic enzyme activities in mouse liver; Biochimica et Biophysica Acta; vol. 919; pp. 111-121; 1987.
Hill et al. Isotope-reinforced polyunsaturated fatty acids protect yeast cells from oxidative stress. Free Radical Biology & Medicine, Jan. 1, 2011, vol. 50, pp. 130-138.
Hill et al; Small amounts of isotope-reinforced polyunsaturated fatty acids suppress lipid autoxidation; Free Radical Biology and Medicine, vol. 53, pp. 893-906; 2012.
Lefkowitz et al; Where Does the Developing Brain Obtain Its Docosahexaenoic Acid? Relative Contributions of Dietary α-Linolenic Acid, Docosahexaenoic Acid, and Body Stores in the Developing Rat; Pediatric Research; vol. 57, No. 1; pp. 157-165; 2005.
Levenson et al; The Healing of Rat Skin Wounds; Annals of Surgery, vol. 161, No. 2; pp. 293-308; Feb. 1965.
Lin et al; Whole body distribution of deuterated linoleic and α-linolenic acids and their metabolites in the rat; Journal of Lipid Research; vol. 48; pp. 2709-2724; 2007.
Rohwedder et al; Measurement of the Metabolic Interconversion of Deuterium-Labeled Fatty Acids by Gas Chromatography/Mass Spectrometry; Lipids; vol. 25, No. 7; pp. 401-405; 1990.
Rosen et al; Effect of Deuterium Oxide on Wound Healing, Collagen and Metabolism of Rats; New England Journal of Medicine; vol. 270, No. 22; pp. 1142-1149; May 28, 1964.
Salem et al; Arachidonic and docosahexaenoic acids are biosynthesized from their 18-carbon precursors in human infants; Proc. Natl. Acad. Sci.; vol. 93; pp. 49-54; Jan. 1996.
Shchepinov et al. Isotope effect, essential diet components, and prospects of aging retardation. Russian Journal of General Chemistry, 2010, vol. 80, No. 7, pp. 1514-1522.
International Search Report and Written Opinion dated Nov. 29, 2012 for PCT/US2012/034832.
International Search Report and Written Opinion dated Nov. 29, 2012 for PCT/US2012/034836.
International Search Report and Written Opinion dated Nov. 29, 2012 for PCT/US2012/034833.
International Search Report and Written Opinion dated Nov. 29, 2012 for PCT/US2012/034835.
Nass et al; Caenorhabditis elegans in Parkinson's Disease Drug Discovery: Addressing an Unmet Medical Need; Molecular Interventions; vol. 8, Issue 6; pp. 284-293; Dec. 2008.
Harman, Denham; Aging and Oxidative Stress; Journal of International Federation of Clinical Chemistry (JIFCC), vol. 10, No. 1; pp. 24-26; Mar. 1998.
Harman, Deham; The Free Radical Theory of Aging; Antioxidants & Redox Signaling; vol. 5, No. 5, pp. 557-561, Oct. 2003.
Hulme et al; Chemistry and the Worm: Caenorhabditis elegans as a Platform for Integrating Chemical and Biological Research; Chemical Biology; Angewandte Chemie International Edition; vol. 50; pp. 4774-4807, 2011.
Adhikary et al., UVA-visible photo-excitation of guanine radical cations produces sugar radicals in DNA and model structures, Nucleic Acids Research, 2005, vol. 33, No. 17, pp. 5553-5564.
Viswanathan and Cushley, Deuterium Nuclear Magnetic Resonance Study of the Interaction of Substrates and Inhibitors with Soybean Lipoxygenase, The Journal of Biological Chemistry, vol. 256, No. 14, pp. 7155-7160, Issue of Jul. 1981.
Yamauchi et al., Observation of the Pathway from Lysine to Isoprenoidal Lipid of Halophilic Archaea, Halobacterium halobium and Natrinema pallidum, Using Regiospecifically Deuterated Lysine, Bull. Chem. Soc. Jpn., vol. 74, pp. 2199-2205 (2001).
Nobuo Tamiya and Takehiko Shimanouchi; Infra-red Absorption spectra of deuterated aspartic acids; Spectrochimica Acta, vol. 18, No. 7, pp. 895-905; Jul. 1, 1962.
Kelly, S et al. "Assessing the authenticity of single seed vegetable oils using fatty acid stable carbon isotope ratios ($^{13}C/^{12}C$)." Food Chemistry. 1997. pp. 181-186. vol. 59, No. 2. Elsevier Science Ltd.
Lichtenstein, A H et al. "Comparison of deuterated leucine, valine and lysine in the measurement of human apolipoprotein A-I and B-100 kinetics." Journal of Lipid Research. 1990. pp. 1693-1702. vol. 31, No. 9.

(56) References Cited

OTHER PUBLICATIONS

International Search Report, May 2007.
Tucker et al. (Journal of Labelled Compounds, vol. VII, No. 1, 1970, pp. 11-15).
Dalle-Donne et al., "Protein carbonylation in human diseases", Elsevier Trends in Molecular Medicine, Apr. 2003, vol. 9, Issue 4, pp. 169-176.
Demidov, V "Heavy isotopes to avert ageing?" Elsevier Trends in Biotechnology, 2007, vol. 25, Issue 9, pp. 371-375.
Shchepinov, M "Reactive Oxygen Species, Isotope Effect, Essential Nutrients, and Enhanced Longevity" Rejuvenation Research, 2007, vol. 10, Issue 1, pp. 1-13.
Finglas et al, Use of an oral/intravenous dual-label stable-isotope protocol to determine folic acid bioavailability from fortified cereal grain foods in women, The Journal of Nutrition, vol. 132, No. 5, pp. 936-939, May 2002.
Geboes et al, Validation of a new test meal for a protein digestion breath test in humans, The Journal of Nutrition, vol. 134, No. 4, pp. 806-810, Apr. 2004.
Notice of Reasons for Rejection dated Aug. 24, 2011 for Japanese Patent Application No. 2008-557833.
Asada et al; Stereochemistry of meso-α,ε Diaminopimelate Decarboxylase Reaction: The First Evidence for Pyriodoxal 5'-Phosphate Dependant Decarboxylation with Inversion of Configuration, Biochemistry, 1981, vol. 20, No. 24, pp. 6881-6886.
Bada et al; Isotopic Fractionation During Peptide Bond Hydrolysis, Geochimica et Cosmoschimica Acta, 1989, vol. 53, pp. 3337-3341.
Balasubramanian et al; DNA strand breaking by the hydroxyl radical is governed by the accessible surface areas of the hydrogen atoms of the DNA backbone. Proc. Natl. Acad. Sci. USA, Aug. 1998, vol. 95 pp. 9738-9743.
Brandl et al; The biosynthesis of 3-(trans-2-Nitrocyclopropyl)alanine, a Constituent of the Signal Metabolite Hormaomycin; European Journal of Organic Chemistry, published online Dec. 20, 2004, vol. 2005, No. 1, pp. 123-135.
Burdzy et al; Synthesis of stable-isotope enriched 5-methylpyrimidines and their use as probes of base reactivity in DNA, Nucleic Acids Research, 2002, vol. 30, No. 18, pp. 4068-4074.
Chiriac et al; Synthesis of [1,3,6,7-15N, 8-13C] adenine; Journal of Labelled Compounds and Radiopharmaceuticals; Apr. 1999 (published online May 4, 1999); vol. 42, issue 4, pp. 377-385.
Cho et al; Cooperativity and anti-cooperativity between ligand binding and the dimerization of ristocetin A: asymmetry of a homodimer complex and implications for signal transduction; Chemistry & Biology; Mar. 1996; vol. 3, issue 3, pp. 207-215.
Esaki et al; Synthesis of base-selectively deuterium-labelled nucleosides by the Pd/C-Catalyzed H-D Exchange Reaction in Deuterium Oxide; Heterocycles; 2005; vol. 66, pp. 361-369.
Foldesi et al; The Synthesis of Deuterionucleosides; Nucleosides, Nucleotides and Nucleic Acids; 2000, vol. 19, No. 10-12, pp. 1615-1656.
Ikeya et al; Evaluation of stereo-array isotope labeling (SAIL) patterns for automated structural analysis of proteins with CYANA, Magnetic Resonance in Chemistry, Jul. 2006, vol. 44, spec. No. S152-S157.
International Search Report and Written Opinion dated Jun. 12, 2007 for PCT/GB2007/050112.
International Search Report and Written Opinion dated Sep. 10, 2010 for PCT/US2009/037173.
International Search Report and Written Opinion dated Dec. 23, 2010 for PCT/US10/54866.
International Search Report and Written Opinion dated Jun. 3, 2009 for PCT/US2009/037161.
Kelland et al; Stereochemistry of Lysine Formation by meso-Diaminopimelate Decarboxylase from Wheat Germ: Use of 1H-13C NMR Shift Correlation to Detect Stereospecific Deuterium Labeling, Biochemistry, Jun. 1985, vol. 24, No. 13, pp. 3263-2367.
Kishore et al; Partial 13C Isotopic Enrichment of Nucleoside Monophosphates: Useful Reporters for NMR Structural Studies; Nucleic Acids Research; Oct. 2005, vol. 33, No. 18.
Knapp et al; Temperature-dependent isotope effects in soybean lipoxygenase-I : Correlating hydrogen tunneling with protein dynamics; JACS Articles; J. Am. Chem. Soc.; vol. 124; pp. 3865-3874; published online Mar. 20, 2002.
Kushner et al; Pharmacological uses and perspectives of heavy water and deuterated compounds; Canadian Journal of Physiology and Pharmacology; Feb. 1999; vol. 77, pp. 79-88.
Oba et al; A simple route to L-[5,5,6,6-D4] lysine starting from L-pyroglutamic acid, Japanese Journal of Deuterium Science, 2006, vol. 12, No. 1, pp. 1-5.
Raap et al; Enantioseletive syntheses of isotopically labeled a-amino acids. Preparation of (ε-13C)-L-α-aminoadipic acid and five isotopomers of L-lysine with 13C, 15N, and 2H in the δ- and ε-positions; Recueil de Travaux Chimiques de Pays-Bas, 1990, vol. 109, No. 4, pp. 277-286.
Rapoport et al; Delivery and turnover of plasma-derived essential PUFAs in mammalian brain; Journal of Lipid Research; May 2001; vol. 42; pp. 678-685.
Ren et al; Simultaneous metabolic labeling of cells with multiple amino acids: localization and dynamics of histone acetylation and methylation, Proteomics: Clinical Applications; Jan. 2007; vol. 1, No. 1, pp. 130-142.
Scholl et al; Synthesis of 5,5,6,6-D4-L-lystine-aflatoxin B1 for use as a mass spectrometric internal standard; Journal of Labelled Compounds & Radiopharmaceuticals; Oct. 2004; vol. 47, No. 11, pp. 807-815.
Svedruzic et al; The Mechanism of Target Base Attack in DNA Cytosine Carbon 5 Methylation; Biochemistry; Aug. 2004; vol. 43, No. 36, pp. 11460-11473.
Tang et al; Kinetic and biochemical analysis of the mechanism of action of lysine 5, 6-aminomutase; Archives of Biochemistry and Biophysics; Oct. 2003; vol. 418, No. 1, pp. 49-54.
The Aldrich Catalog Handbook of Fine Chemicals 2003-2004, p. 141, catalog No. 48, 998-0.
Toyama et al; Assignments and hydrogen bond sensitivities of UV resonance Raman bands of the C8-deuterated guanine ring; Journal of Raman Spectroscopy; Sep. 2002; vol. 33, issue 9, pp. 699-708.
Wade, David; Deuterium isotope effects on noncovalent interactions between molecules; Chemico-Biological Interactions; 1999; vol. 117, No. 3, pp. 191-217.
Written Opinion dated Sep. 8, 2008 for PCT/GB2007/050112.
Chen et al, One-pot selective deuteriation of 5'-dimethoxytritylated deoxynucleotide derivatives, Bioorganic & Medicinal Chemistry Letters, Pergamon, Elsevier Schince, GB, vol. 4, No. 6, pp. 789-794, Mar. 24, 1994.
Extended European Search Report dated Jul. 12, 2011 for EP Application No. 09721095.
Wheeler et al, The synthesis of the 2H, 3H, and 14C-isotopomers of 2'-deoxy-2', 2'-diflourocytidine hydrochloride, an anti-tumor compound, Journal of labelled compounds and radiopharmaceuticals, John Wiley, Chichester, GB, vol. 29, No. 5, pp. 583-589, May 1, 1991.

US 9,320,289 B2

ISOTOPICALLY MODIFIED COMPOUNDS AND THEIR USE AS FOOD SUPPLEMENTS

CROSS REFERENCE TO RELATED APPLICATIONS

This application is a divisional application of the U.S. patent application Ser. No. 12/281,957, filed Aug. 17, 2009 which claims priority to the U.S. National Phase under 35 U.S.C. §371 of International Application No. PCT/GB2007/050112, filed Mar. 8, 2007, which claims priority to United Kingdom Application No. 0604647.8, Filed Mar. 8, 2006. The disclosures of the above-referenced applications are hereby expressly incorporated by reference in their entireties.

FIELD OF THE INVENTION

The present invention related to isotopically modified compounds and their use as food supplements.

BACKGROUND OF THE INVENTION

A currently accepted theory of ageing blames the irreversible changes in cell machinery and reduced efficiency of metabolic processes on the detrimental effects of free radicals and other reactive oxygen species (ROS) or reactive nitrogen species (RNS) which are normally present in the cell as part of the respiratory process. ROS and RNS oxidize/nitrate DNA, proteins, lipids and other cell components. Of these, protein oxidation, which converts arginine, lysine, threonine, thryptophan and proline into corresponding carbonyl compounds, cannot be repaired by proteases after a certain threshold number of amino acid residues have been oxidized.

The damaged protein loses its catalytic or structural activity, but proteases are unable to disintegrate heavily carbonylised strands, so that the damaged species accumulate and aggregate, clogging up cellular passages. This rust-like process gradually wears down all cellular mechanisms, slowing everything down and ultimately causing cellular death.

Apart from ageing, many diseases such as Alzheimer's, Parkinson's, dementia, cataract, arthritis, chronic renal failure, acute repiratory syndrome, cystic fibrosis, diabetes, psoriasis and sepsis, to give a few examples, are associated with increased protein carbonylation. Typically, physiological levels of protein carbonyls are at around 1 nmol/mg protein, whereas pathological levels go to 8 nmol/mg and above.

For the two molecules involved in the process of oxidative damage of proteins, i.e. an oxidizer and its substrate, the oxidizer has been the subject of many studies aiming at neutralizing or removing it by means of increasing the number of antioxidants (vitamins, glutathione, peptides or enzymes). The substrate, e.g. amino acid (AA) residues which are converted into carbonyls, has received less attention.

One common feature of all the AA residues (except proline) vulnerable to carbonylation is that they belong to the group of essential AAs, which cannot be synthesized by vertebrata and should be ingested, e.g. consumed with food. The group includes phenylalanine, valine, tryptophan, threonine, isoleucine, methionine, histidine, arginine, lysine and leucine (arginine is essential for children of up to 5 years of age).

Oxidation of both Arg and Lys by ROS yields aminoadipic semialdehyde and proceeds through sequential replacement of ω-hydrogens with hydroxyls. Oxidation of Lys, Arg, Trp, Thr, Phe and His is shown in FIG. 1. Side-chains undergo the same transformations if these AAs are part of polypeptides/proteins. Other essential AAs undergoing ROS-driven oxidation include Leu (to 5-hydroxyleucine), Val (3-hydroxyvaline) and Ile (several products).

Other types of oxidative damages affecting essential AAs involve reactive nitrogen species (RNS). Examples are shown in FIG. 2.

Yet another process detrimental to proteins is a ROS-driven peptide bond cleavage, which is preceded by oxygen free radical-mediated protein oxidation. A hydrogen atom is abstracted from a $C_\alpha$ atom of the polypeptide chain, which then leads to formation of an alkoxyl radical. This can lead either to hydroxyl protein derivative, or to peptide bond cleavage by (1) diamide or (2) α-amidation pathway. This is illustrated in FIG. 3.

Nucleic acids are not normally considered as essential components of the diet, but are also damaged by ROS. An example particularly important for the mitochondrial functioning is the formation of 8-oxy-G, as illustrated in FIG. 4. This leads to mutations in the mitochondrial genome, which is not maintained and repaired as efficiently as the nuclear genome, with detrimental consequences to the efficiency of respiratory processes in the cell. Another cause of degradation is radiation.

The kinetic isotope effect is widely used when elucidating mechanisms and rate-determining stages of chemical and biochemical reactions. The rate of reaction involving C—$^1$H bond cleavage is typically 5 to 10 times faster than the corresponding C—$^2$H($^2$H=D=deuterium) bond cleavage, due to the two-fold difference in the masses of H and D isotopes. The difference in reaction rates is even higher for tritium ($^3$H or T) as it is 3 times heavier than hydrogen, but that isotope is unstable. The second component of the C—H bond, the carbon atom, can also be substituted for a heavier $^{13}$C isotope, but the bond cleavage rate decrease will be much smaller, since $^{13}$C is only a fraction heavier than $^{12}$C. See Park et al, JACS (2006) 128: 1868-72.

Oxidation reactions are a good example of the isotope effect, as the hydrogen subtraction by an oxidizer is usually a rate-limiting step of the process. Damgaard, Biochemistry (1981) 20: 5662-69, illustrates this: the kinetic isotope effect upon V/K for (1-R)[1-$^2$H$_2$]- and (1-R)[1-$^3$H$_2$]ethanol oxidation by liver alcohol dehydrogenase (ADH) to acetaldehyde, measured at pH 6, was 3 (D(V/K)) and 6.5 (T(V/K)), decreasing to 1.5 and 2.5 respectively at pH 9. Lower than expected rates confirm the discrete role of the non-ADH systems as alternative pathways. In vivo experiments in perfused rat liver, as reported in Lundquist et al, Pharm. & Tox. (1989) 65: 55-62, gave the mean value of D(V/K) of 2.89. Therefore, in all cases the oxidation of deuterated ethanol was substantially slowed down.

Isotopically labelled material has been administered to animals, and also to humans, for diagnostic purposes. Gregg et al, Life Sciences (1973) 13: 755-82, discloses the administration to weanling mice of a diet in which the digestible carbon fraction contained 80 atom % $^{13}$C. The additive was $^{13}$C-labelled acetic acid. Tissue examination revealed no abnormalities clearly attributable to the high isotopic enrichment.

SUMMARY OF THE INVENTION

The present invention is based on the realisation that isotopic substitution can be used to synthesize a class of compounds that, when ingested, result in the formation of bodily constituents (e.g. proteins, nucleic acids, fats, carbohydrates, etc) that are functionally equivalent to normal bodily constituents but which have a greater resistance to degradative/detrimental processes, e.g. those mediated by ROS and RNS or radiation. Therefore, according to this invention, a nutrient composition comprises a nutrient composition comprising an essential nutrient in which at least one exchangeable H atom is $^2$H and/or at least one C atom is $^{13}$C.

Compounds for use in the invention are identical to normal nutrients or constituents of food except that they contain stable isotopes which, when incorporated into bodily constituents make such bodily constituents more resistant to degradative processes than they would be otherwise. They provide a method for protecting the preferred functionality of natural biomolecules; the method comprises supply of a compound in such a way that it becomes incorporated into biomolecules and in so doing confers properties on the biomolecule that protect against damaging or unwanted chemical changes.

Compounds for use in the invention may be chemically synthesized and, when ingested by an organism, are metabolized in a way that results in the incorporation of the compound into a functional biomolecule; the incorporation of the compound resulting in the biomolecule having a higher degree of resistance to damaging molecular changes than would be the case for the equivalent biomolecule that did not comprise the compound. Such compounds may act as mimics of naturally occurring precursor elements of biomolecules. They may mimic an essential amino acid. The organism is typically a plant, microbe, animal or human.

A compound for use in the invention is typically not degraded by enzymes of the P450 pathway. It can therefore accumulate in a subject for which it is essential.

DETAILED DESCRIPTION OF THE PREFERRED EMBODIMENT

The present invention relates to the fact that essential supplements may undergo irreversible chemical transformations such as oxidation, nitration, etc, leading to the onset of senescence or diseases. Essential food components cannot be synthesised de novo by an organism, e.g. mammal, primate or human, and therefore need to be supplied with the diet. For the purposes of this specification, a nucleic acid is essential, although it may be more properly be described as conditionally essential. Conditionally essential nutrients need to be supplied with the diet under certain circumstances.

For humans, 10 amino acids are essential, i.e. Phe, Val, Trp, Thr, Ile, Met, His, Leu, Lys and Arg (up to the age of five). Purine and pyrimidine nucleosides are conditionally essential. Essential fatty acids are ω-3 and ω-6, while monounsaturated oleic acid is generally non-essential.

Figure 1:
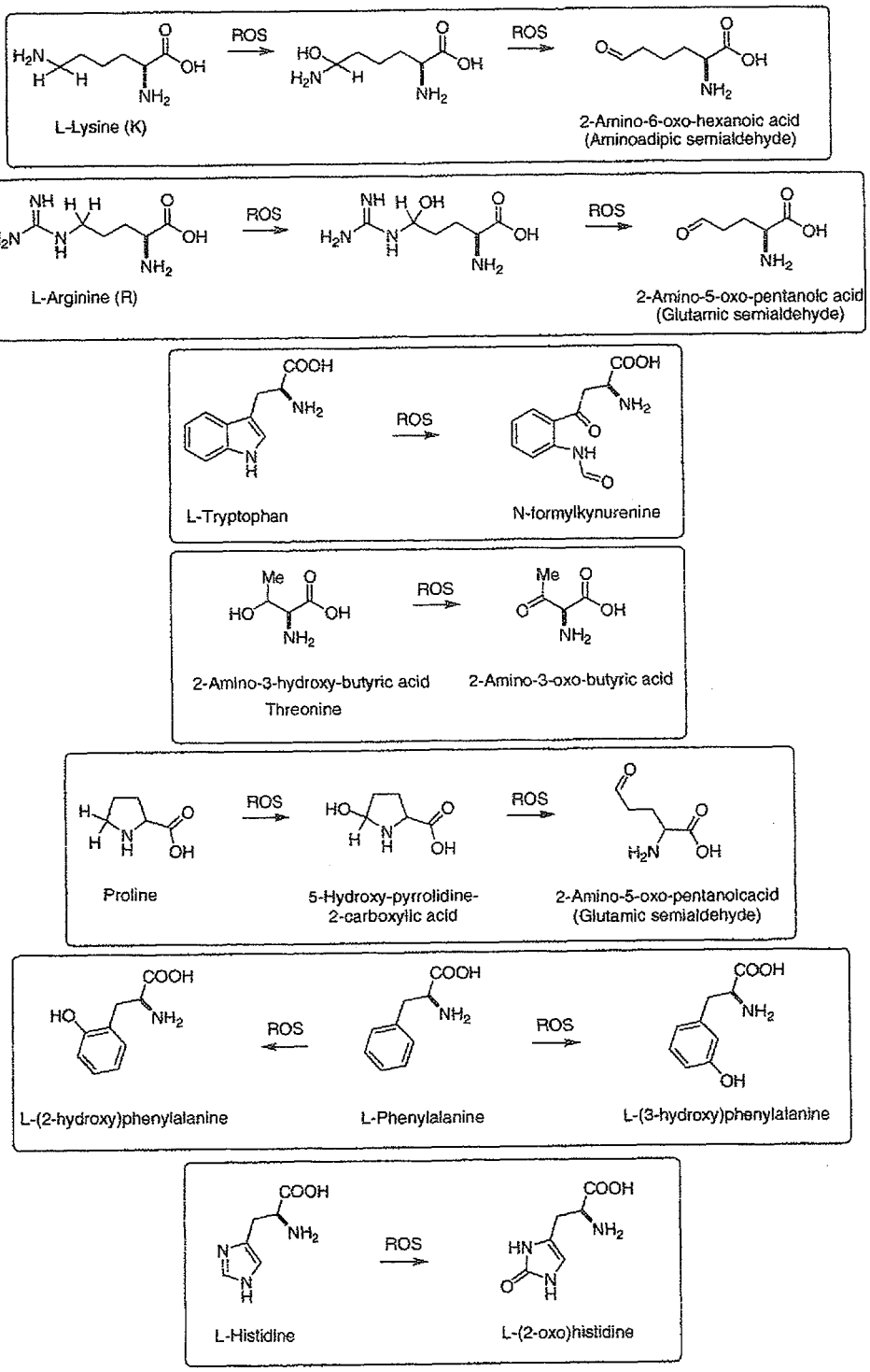
FIGS. 1 to 4 each show reactions that degrade essential nutrients.
Figure 2:
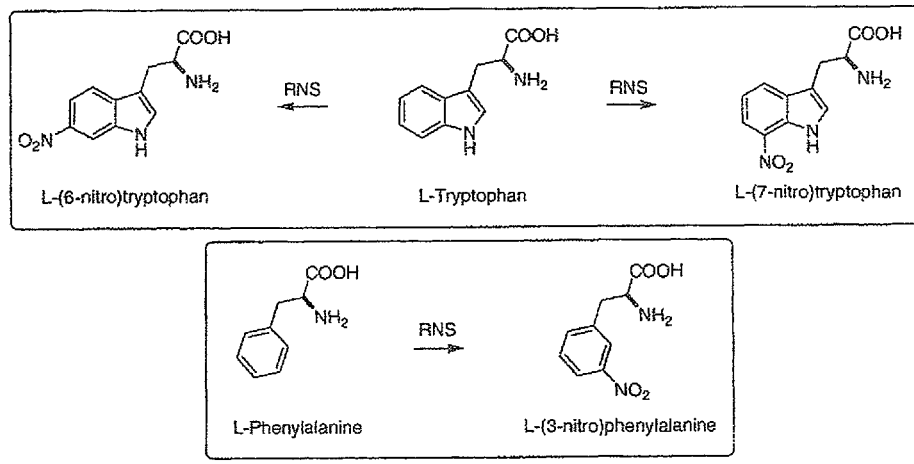
Figure 3:
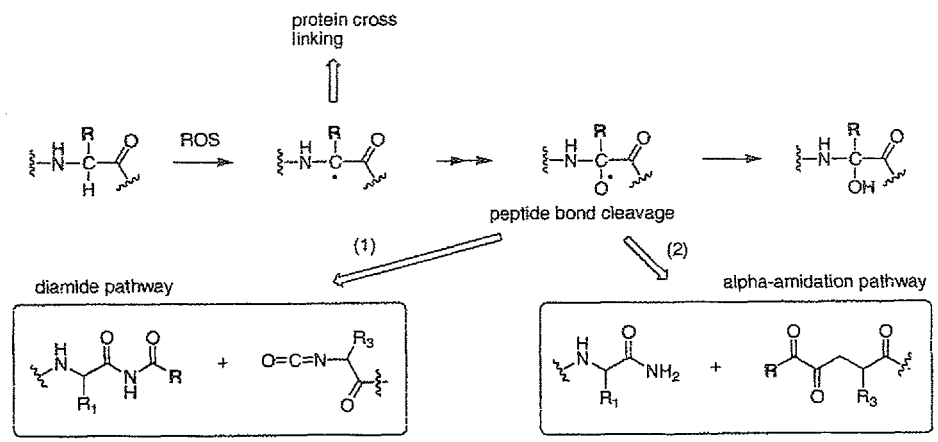
Figure 4:
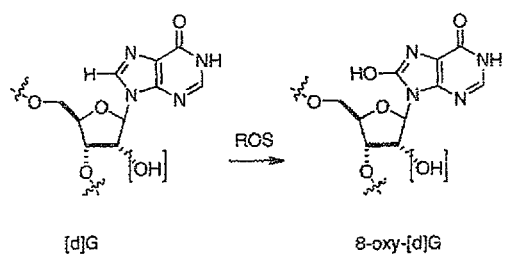

According to this invention, the proposed undesired effects such as ageing/diseases can be slowed down. The compounds consumed should be modified to slow down the undesired reactions, while still retaining their chemical identity. This can be achieved in one embodiment by substituting hydrogen atoms subjected to abstraction during oxidation/oxidative substitution at the most reactive carbon sites, or the sites known to undergo the ROS/RNS inflicted damage as illustrated on FIGS. 1-4, with deuteriums, which due to the isotope effect slow down the rate of reactions. Substituting carbons instead of or in addition to H atom substitution may require a greater degree of substitution since one does not add so much to the reaction rate decrease (D is twice the weight of H, and $^{13}C$ is less than 10% heavier than $^{12}C$).

Depending in part of the method of preparation, a compound for use in the invention may comprise partial or total isotopic substitution. For example, deuterium substitution may be only at the one or two hydrogen atoms that are considered chemically exchangable, e.g. at OH or $CH_2$ adjacent to a functional group. Total rather than partial $^{13}C$ substitution may often be achieved more effectively.

In a preferred embodiment of the invention, the (or only the) oxidation-sensitive hydrogens should be substituted with deuteriums, to minimize the risk of other metabolic processes slowing down when fragments of these AAs are used to build up other structures. In special cases, to further increase the resistance to oxidation, both $^1H$ and $^{12}C$ of a H—C bond can be substituted by $^2H$ and $^{13}C$. To minimize any possible negative effect of isotopes, such as unwanted slowing down of biochemical reactions that utilise fragments of AAs protected with isotopes, preferably only the most sensitive parts of the AAs should be derivatised, for example, ω-atoms of Lys and Arg. Preferred compounds of this type are

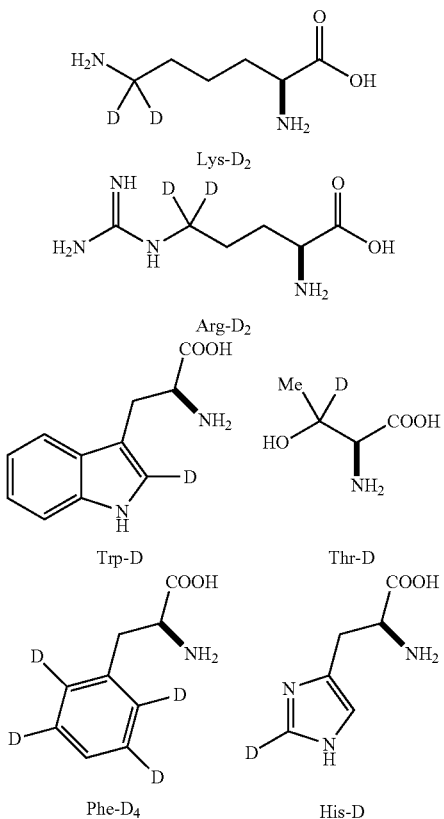

If the oxidative stress is so severe that benefits from protecting the vulnerable sites overweigh potential damaging effects from slowing down other metabolic pathways (as is the case with some diseases), then AAs more heavily protected with isotopes can be employed, as shown in the following, illustrative formulae

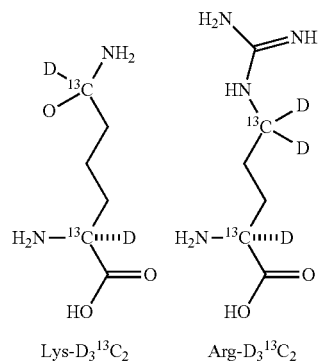

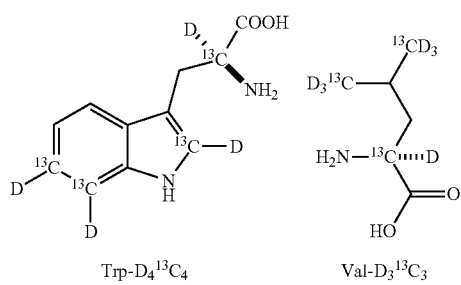

Trp-D$_4$$^{13}$C$_4$    Val-D$_3$$^{13}$C$_3$

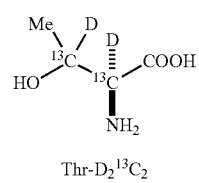

Thr-D$_2$$^{13}$C$_2$

Such derivatives confer protection from the detrimental effects illustrated in FIGS. 1-4.

As all vertebrata have lost the ability to synthesise the essential AAs and require the outside supply of essential AAs or fatty acids, non-painful ways of delivering the deuterated/ deuterated and $^{13}$C-modified AAs into human food sources are possible. For AAs, one example of process is to create essential AAs-deficient yeast/algae/bacteria/etc, growing them on appropriate isotopically 'protected' media/substrates and then feeding the obtained biomass to fish or livestock. The fish or livestock can then be introduced into the food chain in the normal manner. Another example is by a direct pill/supplement-based delivery.

Non-essential components of food are the compounds that can be produced by an organism, such as nucleic acid bases. But when these are consumed as food, some of the non-essential components are digested/used as precursors for other compounds, but a certain fraction is utilized directly in metabolic processes, e.g. nucleic acid (NA) bases, incorporated into DNA. Therefore, as an example, some of the NA bases supplied with food may be isotopically protected, as shown in the following, illustrative formulae

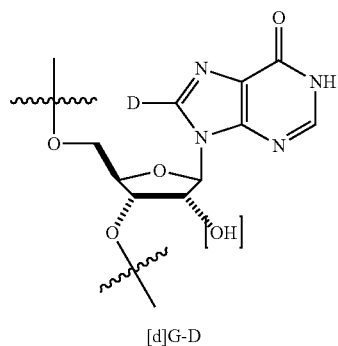

[d]G-D

[d]G-D, $^{13}$C

Such species are less vulnerable to oxidation upon incorporation into DNA. In other words, the oxidation rate of DNA, including mitochondrial DNA, can be reduced.

Both essential and non-essential components may be administered through a digestive system to achieve a desired effect of slowing down detrimental changes associated with ageing process and various diseases. Nevertheless, ways other than through the digestive tract, for instance intravenous delivery, can be envisaged. The important aspect of any delivery system is to get the isotopically engineered compounds incorporated into bodily/biochemical constituents.

A composition of the invention can be provided like any food supplement. It typically comprises one or more nutrient; in addition to the isotopically labelled essential component. It may comprise plant material, microbial material or animal material. The composition may be a normal foodstuff, a tablet or other solid medicament, or an injectable or other liquid.

The composition may comprise unmodified compounds in addition to those that have been labelled. The labelled compound is typically present in a larger amount, and certainly greater than that which may be present naturally.

Compounds for use in the invention may be prepared by procedures that are known or that can be modified as appropriate by one of ordinary skill in the art, For example, the deuterated analogue of Lys, 2,6-diaminohexanoic acid-6,6-D$_2$, may be synthesized from a precursor nitrile by hydrogenolysis in D2 according to standard procedures.

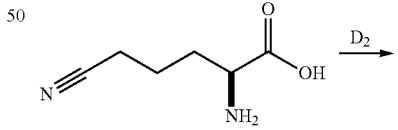

(S)-2-amino-5-cyanopentanoic acid

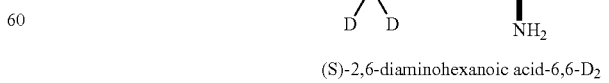

(S)-2,6-diaminohexanoic acid-6,6-D$_2$

The deuterated analogue of Arg, 2-amino-5-guanidinopentanoic acid-5,5-Z)2, may be synthesized from a corresponding nitrile.

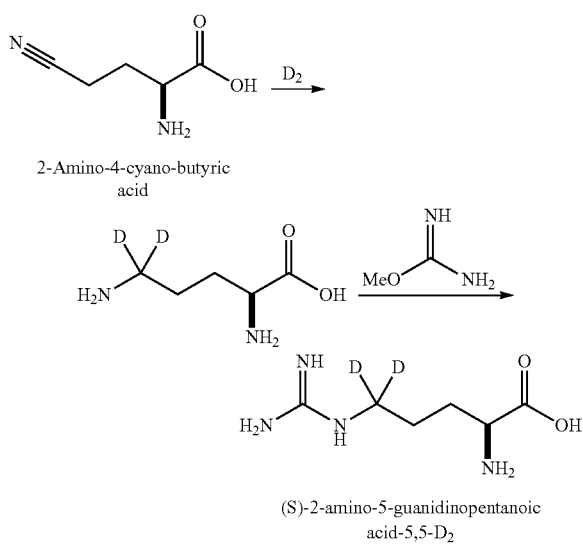

2-Amino-4-cyano-butyric acid (S)-2-amino-5-guanidinopentanoic acid-5,5-D$_2$

Ornithine-D$_2$, obtained by hydrogenolysis in a way similar to that described above for Lys, was dissolved in water and mixed with an equal volume of 0.5M 0-methylisourea, pH 10.5, adjusted with NaOH. After 4-5 h, 1% TFA was added to stop the reaction. The compound was purified by a RP HPLC (Buffers were A: 0.1% TFA/H$_2$O; B: 0.1% TFA (80% MeCN/20% H$_2$O)), 0-65% B over 40 min. See Kimmel, Methods Enzymol. (1967), 11:584-589, and Bonetto et al, Anal. Chem. (1997), 69: 1315-1319.

Cyano-aminoacids are precursors to amino acids. Synthesis of cyano-aminoacids can be carried out by several routes, starting from a variety of precursors. Alcohols (Davis & Untch, J. Org. Chem. (1981); 46: 2985-2987), amines (Mihailovic et al, Tet. Lett. (1965) 461-464), amides (Yamato & Sugasawa, Tet. Lett. (1970) 4383-4384) and glycine (Belokon et al, JACS (1985)107: 4252-4259) can all serve as starting materials in such syntheses. Some methods can yield both $^{13}$C and $^2$H-substituted compounds, while others are only compatible with deuteration.

Deuteration can be carried out using deuterium gas (for example, as described in White et al, JACS (1994) 116: 1831-1838) or different deuterides, for example NaBD$_4$ (Satoh et al, Tet. Let. (1969) 4555-4558); the choice between these methods should be made based on the availability and price of the corresponding deuterium derivatives. Some of the strategies tested are described in detail below.

The sites to be protected within essential fatty acids for the purpose of the present invention are the methylene groups of the 1,4-diene systems ('bis-allyl' positions). They are the most reactive, and can easily be derivatised using a variety of methods. Bromination of this position followed by reduction with $^2$H$_2$ results in the substitution of one hydrogen at a time. To substitute both, the procedure should be repeated twice. A more attractive method may be a direct one-step substitution in heavy water. An example of such exchange is given below (Example 6) for 8-deuteration of deoxyguanosine.

An alternative approach to the synthesis of deuterated unsaturated fatty acids is based on strong base treatment of 1,4-dienes followed by quenching with heavy water. This is illustrated in Example 7.

There are literature examples for substitutions at any position for all major nucleotide bases, with all major types of isotopes ($^2$H$_2$, $^3$H$_2$, $^{13}$C, $^{14}$C, $^{15}$N, $^{18}$O etc). Described below are just two procedures, based on the previously published work, for selective deuteration of purines (Esaki et al, Heterocycles (2005) 66: 361-369, and Chiriac et al, Labelled Compd. Radiopharm (1999) 42: 377-385). Numerous other protocols are suitable as well. It is often possible to exchange hydrogens for deuteriums on an existing nucleic acid base/nucleoside, while to incorporate $^{13}$C, the bases should be assembled (for example, see Folesi, et al, Nucleosides Nucleotides Nucleic Acids (2000).

Syntheses of some isotopically 'reinforced' essential dietary components suitable for use in the present invention are known; see for instance, 6,6-$^2$H$_2$,1,1-$^{13}$C$_2$-L-Lys: Lichtenstein et al, J. Lipid Res. (1990) 31: 1693-1701 and 8-deutero-deoxy-guanosine: Toyama et al, J. Raman Spectrosc. (2002) 33: 699-708).

The invention is not limited by the synthetic organic chemistry methods described above, as there exists a large arsenal of different methods that can also be used to prepare the above mentioned and other isotopically protected components suitable for use in the present invention. For instance, in addition to the methods disclosed in the Examples, other methods suitable for conversion of a primary amino group function into a CN function (with the aim of subsequent deuteration of the alpha-(relative to N) carbon atom) can be employed, such as:

a direct oxidation by oxygen catalysed by cuprous chloride-dioxygen-pyridine system (Nicolaou et al, Synthesis (1986) 453-461; Capdevielle et al, Tet. Lett. (1990) 31: 3305-3308)

a direct conversion using bromosuccinimide (Gottardi, Monatsh. Chem. (1973) 104: 1690-1695)

a direct iodosobenzene oxidation (Moriarty et al, Tet. Lett. (1988) 29: 6913-6916)

a two-step conversion via a di-tosyl derivative and an iodo derivative (DeChristopher et al, JACS (1969) 91: 2384-2385).

The following Examples 1 to 9 illustrate the preparation of materials suitable for use in the invention.

(MA) LDI-TOF mass spectra were obtained using a Voyager Elite Biospectrometry Research Station (PerSeptive Biosystems, Vestec Mass Spectrometry Products) in a positive ion mode; FAB spectra were acquired using a Varian instrument. Analytical thin-layer chromatography was performed on the Kieselgel 60 F$_{254}$ precoated aluminium plates (Merck) or aluminium oxide 60 F$_{254}$ precoated aluminium plates (Merck), spots were visualized under UV or as specified. Column chromatography was performed on silica gel (Merck Kieselgel 60 0.040-0.063 mm) or aluminium oxide (Aldrich aluminium oxide, activated, neutral, Brockmann I, 150 mesh, 58 Å).

Reagents for biological experiments, unless otherwise specified, were from Sigma-Aldrich. $^{13}$C-glucose was from Sigma and Reakhim (Russia).

Reagents obtained from commercial suppliers were used as received. All solvents were from Aldrich; trifluoroacetic acid was from Pierce; HPLC grade solvents were from Chimmed (Russia), and were used without further purification. (S)-2-Amino-5-cyanopentanoic acid was from Genolex (Russia). Deuterium gas was generated by electrolysis by a GC Hydrogen Supply Module (output 6 atm; Himelectronika, Moscow, Russia), using heavy water as a source. Heavy water ($^2$H$_2$O, D$_2$O), NaBD$_4$ and Na$^{13}$CN were from Reakhim (Russia) and Gas-Oil JSC (Russia). DMF was freshly distilled under reduced pressure and stored over 4 Å

Example 1

(S)-2-Amino-4-cyano($^{13}$C)-butyric acid (a precursor for $^{13}$C-Arg and $^{13}$C, $^2$H$_2$-Arg

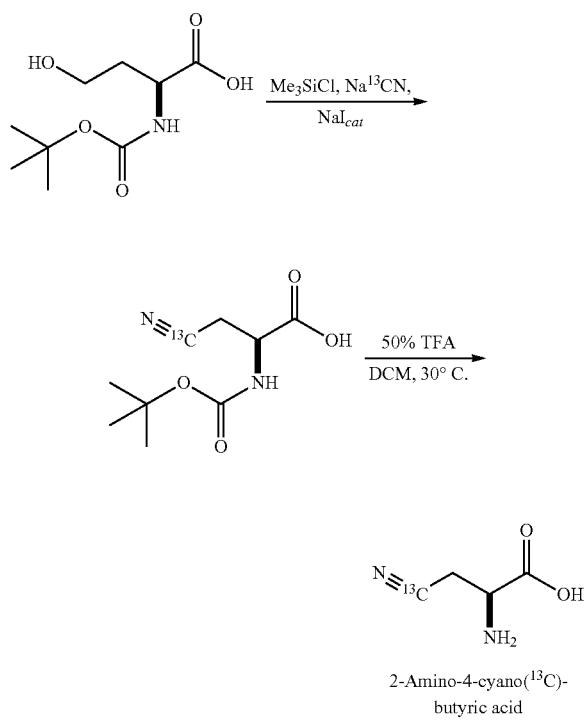

2-Amino-4-cyano($^{13}$C)-butyric acid 2.19 g (10 mmol) of N-Boc-homo-Serine (Bachem; desiccated overnight over P2O5) was dissolved in 10 ml of a mixture of acetonitrile/dimethylformamide (1:1). Dry Na $^{13}$CN (Gas-Oil JSC, Russia; 1 g, 2 eqv) and NaI (10 mg, cat) were added, and the mixture was degassed. Me$_3$SiCl (2.55 ml, 2 eqv) was then added with a syringe at RT under argon. The reaction mixture was stirred under argon at 60° C. for 6 h, with monitoring by TLC (chloroform/methanol 2:1, visualization in iodine vapor). Upon completion, the reaction mixture was cooled to RT, diluted with water (100 ml) and extracted with diethyl ether (2×50 ml). The organic phase was washed with water (4×50 ml) and brine (50 ml), dried (Na$_2$SO$_4$), decanted and concentrated in vacuo to yield (2.07 g, 91%) of colorless oil. The structure of the Boc-nitrile was confirmed by MALDI-TOF (Voyager Elite, PerSeptive Biosystems), with HPA as a matrix. Found: 229.115 (MI), 230.114 (MI+H$^+$), 252.104 (MI+Na$^+$). No peaks related to the starting material were detected.

The removal of the Boc protecting group and the work-up were carried out using a standard peptide synthesis protocol (50% TFA in DCM, 30 min, RT). The structure of the nitrile was confirmed by MALDI-TOF (Voyager Elite, PerSeptive Biosystems), with HPA as a matrix. Found: 129.062 (MI), 130.070 (MI+H$^+$). No signal related to the starting material was detected.

Example 2

(S)-2-Amino-4-cyano-butyric acid (a precursor for $^2$H$_2$-Arg)

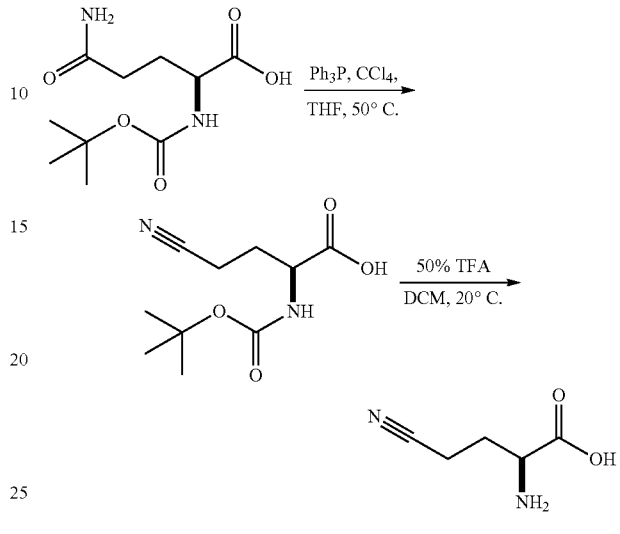

4.93 g (20 mmol) of N-Boc-L-Glutamine (Sigma) was dissolved in 30 ml of anhydrous THF and added with stirring to a mixture of triphenylphosphine (10.49 g, 40 mmol, Aldrich) and 40 ml of anhydrous tetrachloromethane. The reaction mixture was stirred with gentle heating for 3 h (control by TLC, chloroform/methanol 2:1, visualization in iodine vapour), cooled and the precipitate of triphenylphosphine oxide filtered off. The oil obtained upon evaporation and re-evaporation with an additional 15 ml of THF was diluted with 30 ml of water. The aqueous fraction was saturated with brine, washed with diethyl ether (2×20 ml), and acidified to pH 3.5 with sulphuric acid. The product was extracted with ethyl acetate (2×20 ml). Combined organic fractions were dried (brine, Na$_2$SO$_4$) decanted and evaporated to give 3.46 g (76%) of colorless oil. The structure of the Boc-nitrile was confirmed by MALDI-TOF (Voyager Elite, PerSeptive Biosystems), with HPA as a matrix. Found: 228.114 (MI), 229.114 (MI+H+), 251.103 (MI+Na+)_No peaks related to the starting material were detected.

The removal of the Boc protecting group and the work-up were carried out using a standard peptide synthesis protocol (50% TFA in DCM, 30 min, RT). The structure of the nitrile was confirmed by MALDI-TOF (Voyager Elite, PerSeptive Biosystems), with HPA as a matrix. Found: 128.069 (MI), 129.075 (MI+H$^+$). No signal related to the starting material was detected.

Example 3

Lys-$^2$H$_2$

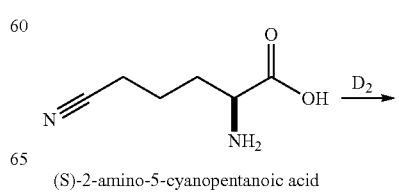

(S)-2-amino-5-cyanopentanoic acid

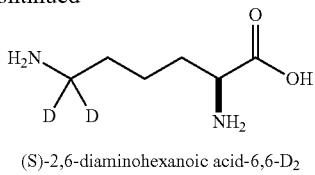

(S)-2,6-diaminohexanoic acid-6,6-D₂

(S)-2-amino-5-cyanopentanoic acid (Genolex, Russia; 14.21 g, 100 mmol) was dissolved in 100 ml of methanol. To this, Raney nickel, prepared from 4 g of alloy (30% Ni) according to (Adkins H. et al, Org. Syntheses. Coll. Vol. III, 1955, p. 180) was added, and the reaction mixture was shaken under deuterium (100 atm) at 90° C. for 24 h. (TLC: n-butanol-pyridine-acetic acid-water: 15-10-3-12; visualization by iodine vapor and fluorescamine). The reaction mixture was filtered and evaporated in vacuo. The product was redissolved in water-ethanol (3:1; 20 ml) followed by evaporation in vacuo (×4) and then crystallized from ethylacetate to give 11.55 g (78%) of the deuterated product. The structure of deuterated lysine was confirmed by MALDI-TOF (Voyager Elite, PerSeptive Biosystems), with HPA as a matrix. Found: 148.088 (MI), 149.089 (MI+H⁺).

Example 4

(5-$^{13}$C, 5,5-$^2$H)-Arginine

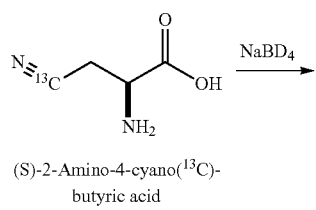

(S)-2-Amino-4-cyano($^{13}$C)-butyric acid (S)-2-amino-5-guanidino pentanoic acid-5-$^{13}$C,5,5-D₂

The (S)-2-Amino-4-cyano($^{13}$C)-butyric acid (182 mg, 1.41 mmol) and CoCl₂×6H₂O (Aldrich, 670 mg, 2.82 mmol) were dissolved in water (6 ml) and NaBD₄ (Reakhim, Russia; 540 mg, 14.1 mmol) was added in two portions over 20 min. The nitrile was reduced in 30 min (control by TLC: n-butanol-pyridine-acetic acid-water: 15-10-3-12; fluorescamine/UV detection for Boe-protected amino acids, iodine vapor visualization for unprotected amino acids).

The reaction mixture was quenched by acidification (IM HCl) followed by acetone, and purified by ion exchange (Amberlite IR120P (H⁺), Aldrich). The column was washed with water till neutral pH. The product was then recovered by washing the column with NH40H (0.3 M) followed by evaporation. The resulting omitine-$^{13}$C, $^2$H₂ (yield: 158 mg, 83%; MALDI-TOF (Voyager Elite, PerSeptive Biosystems), with HPA matrix. Found: (MI), 136.068 (MI+H⁺) was dissolved in water and mixed with an equal volume of 0.5M O-methylisourea (Kimmel, supra), pH 10.5, adjusted with NaOH. After 4-5 h 1% TFA was added to stop the reaction (Bonetto et al, supra). The compound was purified by a RP HPLC (Buffers were A: 0.1% TFA/H₂O; B: 0.1% TFA/(80% MeCN/20% H₂O)), 0-65% B over 40 min to give 140 mg (68%) MALDI-TOF (Voyager Elite, PerSeptive Biosystems), with HPA matrix; found: 177.402 (MI), 178.655 (MI+H⁺).

Example 5

5-(5,5-$^2$H₂)-Arginine

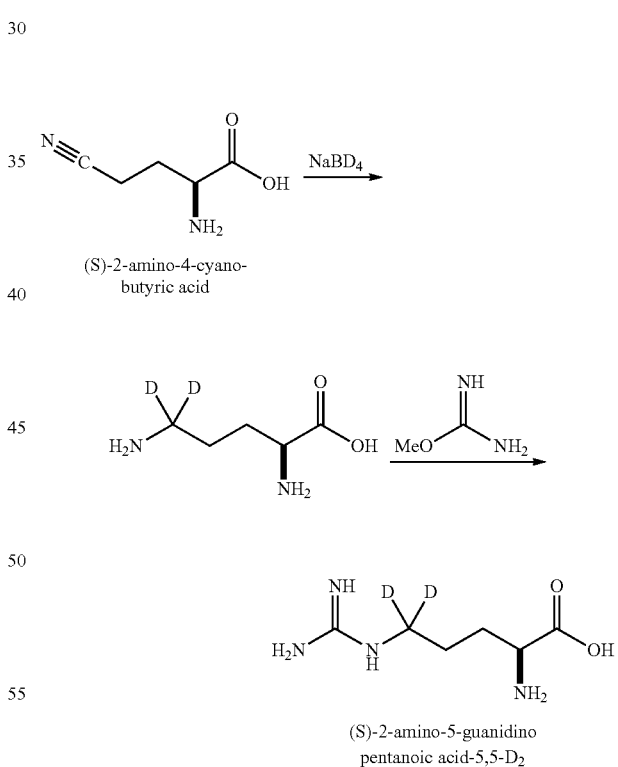

(S)-2-amino-4-cyano-butyric acid (S)-2-amino-5-guanidino pentanoic acid-5,5-D₂

The title compound was synthesized using the above protocol, starting from (S)-2-amino-4-cyano-butyric acid (Technohim, Russia). MALDI-TOF (Voyager Elite, PerSeptive Biosystems), with HPA matrix; found: 176.377 (MI), 177.453 (MI+H⁺).

Example 6

11,11-di-deutero-linoleic acid (18:2)

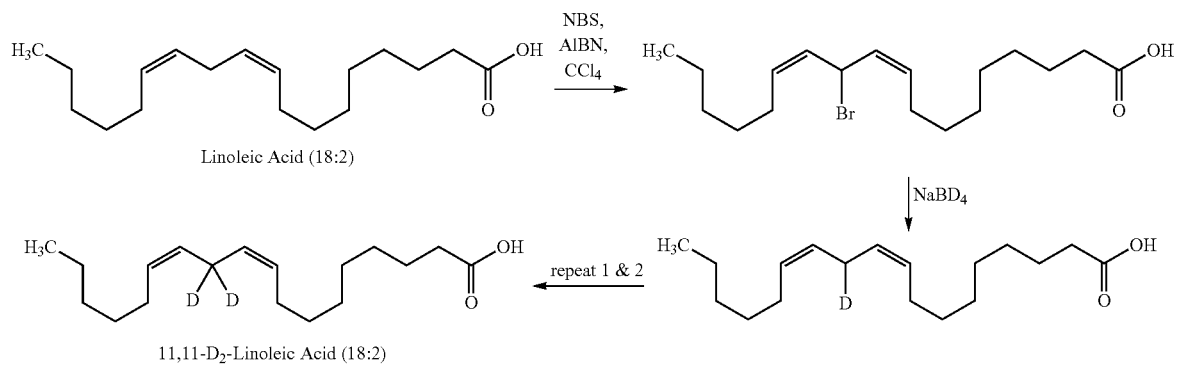

Linoleic acid (7 g, 25 mmol, Aldrich) was dissolved in 25 ml of carbon tetrachloride dried over $P_2O_5$. N-bromosuccinimide (4.425 g, 25 mmol, desiccated overnight over $P_2O_5$) and 0.05 g AIBN were added, and the reaction mixture in a flask with a reversed condenser was stirred with gentle heating till the reaction was initiated as manifested by an intense boiling (if the reflux is too intense the heating should be decreased). When succinimide stopped accumulating on the surface, the heating was continued for another 15 min (about 1 h in total). The reaction mixture was cooled to RT and the precipitate filtered off and washed with $CCl_4$ (2×5 ml). The combined organic fractions were evaporated and the 11-Bromolinoleic acid obtained was gradually added to a solution of NaBD4 (390 mg, 10 mmol) in 30 ml of isopropanol. After an overnight stirring, a diluted solution of HCl was slowly added till there was no more deuterium gas produced. Upon a standard workup, the mono-deuterated acid was brominated and reduced again to yield a target di-deutero derivative (bp 230-231° C./15 mm, 4.4 g, 63%). MALDI-TOF MS: mono-bromo derivative, found: 358.202, 360.191 (doublet, approx 1:1, MI); di-deutero delivative, found: 282.251 (MI).

Example 7

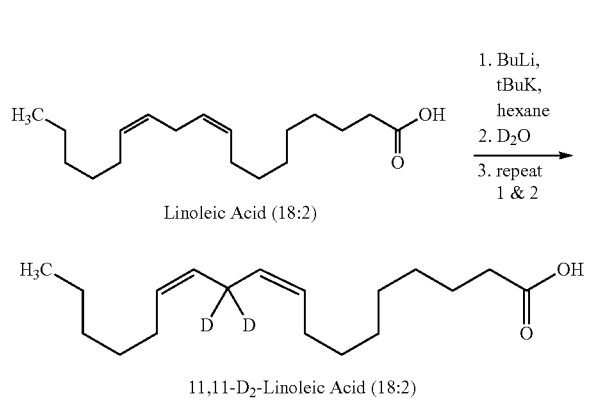

11,11-$D_2$-Linoleic acid (18:2) was synthesized by treating linoleic acid with an eqv of a BuLi-tBuK (Sigma-Aldrich) mix in hexane followed by quenching with $D_2O$. To improve yields this procedure needs to be repeated 3-4 times. It was found that this procedure also generates a detectable amount of alpha-deuterated product (FAB MS, Xe ions, thioglycerine: found: 283.34 (72; MI+1)$^+$, 284.33 (11; alpha-monodeuteroderivative, MI+1)$^+$285.34 (10; alpha-dideuteroderivative, MI+I)$^+$; the nature of '284' and '285' peaks was established using MS/MS. The substitution at alpha-position can be prevented by utilizing transient ortho-ester protection (Corey & Raju Tetrahedron Lett. (1983) 24: 5571), but this step makes the preparation more expensive.

Example 8

8-D-Deoxyguanosine from Deoxyguanosine

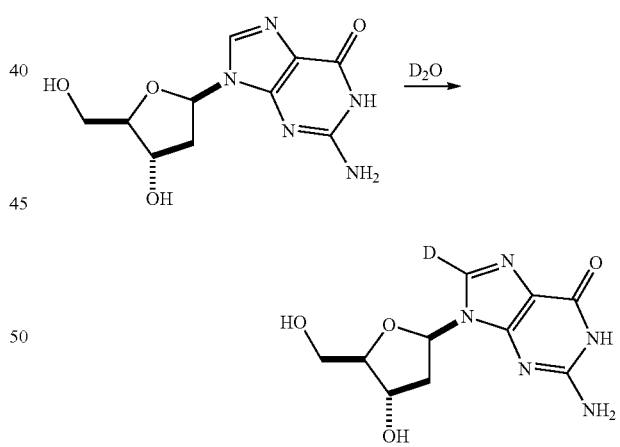

Deoxyguanosine (268 mg, 1 mmol, Aldrich) was dissolved in 4 ml of $D_2O$. 10% Pd/C (27 mg, 10 wt % of the substrate, Aldrich) was added, and the mixture was stiffed at 160° C. in a sealed tube under H2 atmosphere for 24 h. After cooling to RT, the reaction mixture was filtered using a membrane filter (Millipore Millex®-LG). The filtered catalyst was washed with boiling water (150 ml), and the combined aqueous fractions were evaporated in vacuo to give deoxyguanoside-d as a white solid (246 mg, 92%). The structure of the nucleoside was confirmed by MALDI-TOF (Voyager Elite, PerSeptive Biosystems), with HPA as a matrix. Found: 268.112 (MI).

Example 9

8-D-Deoxyguanosine from 8-bromodeoxyguanosine

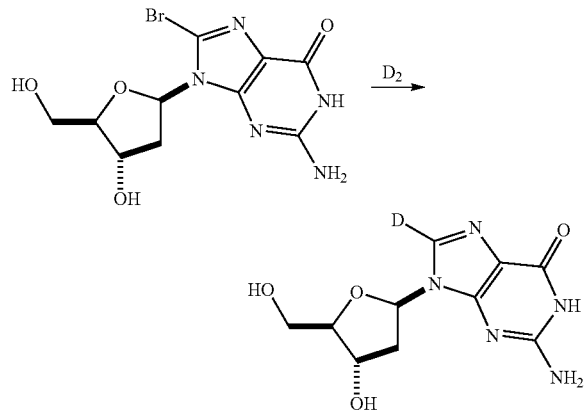

7% Pd/C catalyst, prepared from PdCl2 as described in Chiriac et al (1999) 42: 377-385, was added to a solution of 8-bromodeoxyguanosine (Sigma) and NaOH in water. The mixture was stirred in $D_2$ (2 atm) at 30° C. The catalyst was filtered off and the reaction mixture was neutralized with 2N HCl. The procedure provides approx. 85-90% yield of the product. Other reducing agents can be employed, such as $NaBD_4$ (see the synthesis of D,D-linoleic acid).

The following Examples 10 to 12 illustrate the utility of the invention. In order to establish a range of a potential heavy isotope substitutions for the invention (from 100% light isotope to 100% heavy isotope, as well as the localized site protection such as that shown in FIGS. 1-4, using compounds as shown above), and to test for a possible toxicity of large amounts of heavy isotopes on an organism, the influence of heavy carbon ($^{13}C$) and specifically 'protected' building blocks of biopolymers (nucleic acid components (nucleosides), lipids and amino acids) on the life span was tested on a nematode Caenorhabditis elegans.

Previous studies of the model organism C. elegans have almost exclusively employed cultivation on a bacterial diet. Such cultivation introduces bacterial metabolism as a secondary concern in drug and environmental toxicology studies (specific metabolite-deficient bacterial strains can be employed to evaluate the influence of particular essential nutrients on the nematode longevity). Axenic cultivation of C. elegans can avoid these problems, yet some earlier work suggests that axenic growth is unhealthy for C. elegans. (Szewczyk et al, Journal of Experimental Biology 209, 4129-4139 (2006)). For the present invention, both NGM and axenic diets were employed in combination with isotopically enriched nutraceutical components.

Example 10

$^{13}C_6$-glucose (99% enrichment; Sigma) was used as a carbon food source for culturing of Escherichia coli; the control was identical except for the $^{12}C_6$-glucose. C. elegans (N2, wild type) were grown on a standard (peptone, salts and cholesterol) media seeded with Escherichia coli prepared as described above. The only carbon-containing component apart from E. coli was $^{12}C$-cholesterol (Sigma; a hormone precursor that is essential for C. elegans), since the corresponding $^{13}C$-derivative was unavailable. Nematodes were thus grown on a 'heavy' and 'light' (control) diet in the temperature range of 15-25° C., in pools of 50-100 worms each. The animals on both diets developed normally with all major characteristics being very similar.

The longevity data was analyzed using Prism software package (GraphPad software, USA), according to published procedures (Larsen et al, Genetics 139: 1567 (1995)). It was found that animals on the 'heavy' diet have an increase of a lifespan of around 10% (in a typical experiment, 14 days for $^{12}C$ animals versus about 15.5 days for the $^{13}C$-fed worms, for 25° C.).

Example 11

Basic composition of the axenic media used was adapted from (Lu & Goetsch Nematologica (1993) 39: 303-311). Water-soluble and TEA-soluble components (vitamins and growth factors), salts, non-essential amino acids, nucleic acid substituents, other growth factors and the energy source were prepared as described (0.5 L of 2x). To this, a mix of essential amino acids was added, containing (for 0.5 L as 2x): 0.98 g L-($D_2$)-Arg (see above); 0.283 g L-Hys; 1.05 g L-($D_2$)-Lys (see below); 0.184 g L-Trp; 0.389 g L-Met; 0.717 g L-Thr; 1.439 g L-Leu; 0.861 g L-Ile; 1.02 g L-Val, and 0.623 g L-Phe. Prior to adding to the remaining components, this mixture was stirred at 55° C. for 4 hours until a clear solution was formed, and then cooled to room temperature.

C. elegans (N2, wild type) were cultivated on this medium. For the control experiment, nematodes were grown on a medium prepared as above but containing standard L-Arg and L-Lys instead of the deuterated analogues, in the temperature range of 15-25° C., in pools of 50-100 worms each. The longevity data was analyzed using Prism software, as described in Example 10.

Example 12

A $^{12}C$-NGM diet was enriched with 5,5-di-deutero-arginine and 6,6-di-deutero-lysine, 11,11-di-deutero-linoleic acid (18:2), and 8-D-deoxyguanosine. C. elegans were grown on a standard (peptone, salts and cholesterol) medium seeded with Escherichia coli prepared as described above, to which deuterium-'reinforced' derivatives (see above) were added. to a total concentration of 1 g/L of each deuterated compound. Nematodes were thus grown on a 'heavy' and 'light' (control—whereby non-deuterated L-Arginine, L-Lysine, linoleic acid (18:2), and deoxyguanosine were used instead of deuterated analogues in 1 g/L concentrations) diet in the temperature range of 15-25° C., in pools of 50-100 worms each. The longevity data was analyzed using Prism software package, as described in Example 10.

The invention claimed is:

1. A foodstuff, comprising an isotopically modified component and non-isotopically modified fatty acid or fat;
    wherein the isotopically modified component is a fatty acid or fat that is isotopically modified at least at one or more bis-allylic positions;
    wherein the amount of the isotopically modified component is at least 0.1% of the foodstuff;
    wherein the amount of the isotopically modified component is sufficient to reduce the extent of lipid oxidation in a patient; and
    wherein the ratio of the fatty acid or fat that is isotopically modified to the non-isotopically modified fatty acid or fat is greater than 1:1.

2. The foodstuff of claim 1, wherein amount of the isotopically modified component is sufficient to significantly reduce lipid oxidation mediated by free radicals, reactive oxygen species, reactive nitrogen species, or radiation in the subject.

3. The foodstuff of claim 2, wherein the amount of the isotopically modified component is sufficient to significantly reduce lipid oxidation mediated by free radicals.

4. The foodstuff of claim 1, wherein the isotopically modified component resists degradation initiated by enzymes of the P450 pathway.

5. The foodstuff of claim 1, wherein the isotopically modified component or metabolite thereof is a fatty acid that is an essential food component.

6. The foodstuff of claim 1, wherein the fatty acid or fat is isotopically modified at one bis-allylic position.

7. The foodstuff of claim 6, wherein the fatty acid is 11-D-linoleic acid or 11,11-$D_2$-linoleic acid.

8. The foodstuff of claim 7, wherein the fatty acid is 11,11-$D_2$-linoleic acid.

9. The foodstuff of claim 1, wherein the isotopic modification comprises at least one $^{13}C$ atom or at least one deuterium atom at the one or more bis-allylic positions, wherein the at least one $^{13}C$ atom or the at least one deuterium atom are present at a level significantly above the naturally-occurring abundance level of said isotope in said fatty acid.

10. The foodstuff of claim 9, wherein the isotopically modified fatty acid is 11-D-linoleic acid or 11,11-$D_2$-linoleic acid.

11. The foodstuff of claim 10, wherein the isotopically modified fatty acid is 11-D-linoleic acid.

12. The foodstuff of claim 1, wherein the fatty acid is a polyunsaturated substance.

13. The foodstuff of claim 1, wherein the isotopically modified fatty acid is 11-D-linoleic acid or 11,11-$D_2$-linoleic acid.

14. The foodstuff of claim 13, wherein the isotopically modified fatty acid is 11-D-linoleic acid.

15. The foodstuff of claim 1, wherein the fatty acid is a carboxylic acid.

16. The foodstuff of claim 1, wherein the foodstuff is suitable for human consumption.

17. The foodstuff of claim 1, wherein the deuterium replaces a hydrogen at an oxidation-sensitive site of the fatty acid or fat or at a site that becomes oxygen sensitive upon enzymatic desaturation or elongation.

18. The foodstuff of claim 1, further comprising an isotopically modified amino acid or nucleic acid base in an amount of at least 0.1% of the foodstuff.

* * * * *